United States Patent [19]

Wood, Jr. et al.

[11] Patent Number: 5,420,274

[45] Date of Patent: May 30, 1995

[54] PROCESS FOR THE PREPARATION OF 2,4-DI(ALKYLAMINO)-6-ALKYLTHIO-S-TRIAZINES

[75] Inventors: Mervin G. Wood, Jr., Satsuma; Henry C. Grace, Saraland, both of Ala.

[73] Assignee: Ciba-Geigy Corporation, Ardsley, N.Y.

[21] Appl. No.: 138,858

[22] Filed: Oct. 19, 1993

[51] Int. Cl.⁶ .................. C07D 251/38; C07D 251/40; C07D 251/52

[52] U.S. Cl. .................... 544/213; 544/211; 544/212; 544/208; 544/209; 544/210

[58] Field of Search .............. 544/213, 212, 211, 208, 544/209, 210

[56] References Cited

U.S. PATENT DOCUMENTS

| | | | |
|---|---|---|---|
| 3,629,256 | 12/1971 | Berrer et al. | 260/249.8 |
| 3,741,745 | 6/1973 | Berrer et al. | 71/93 |
| 3,746,710 | 7/1973 | Kühne et al. | 260/249.8 |
| 3,753,986 | 8/1973 | Singhal et al. | 260/249.8 |
| 3,766,182 | 10/1973 | Kühne et al. | 260/24.98 |
| 3,830,810 | 8/1974 | Berrer et al. | 260/249.8 |
| 4,220,770 | 9/1980 | Gass | 544/208 |
| 4,242,119 | 12/1980 | Berrer et al. | 71/67 |
| 4,260,753 | 4/1981 | Berrer et al. | 544/208 |
| 4,883,871 | 11/1989 | Coers | 544/210 |
| 5,099,017 | 3/1992 | Eberspach et al. | 544/198 |

FOREIGN PATENT DOCUMENTS

| | | |
|---|---|---|
| 0357556 | 3/1990 | European Pat. Off. |
| 0398843 | 11/1990 | European Pat. Off. |
| 0413999 | 2/1991 | European Pat. Off. |

OTHER PUBLICATIONS

Aldrichimica Acta, vol. 9, No. 3, 1976 (pp. 35–45) Jones.

Aldrichimica Acta, vol. 13, No. 3, 1980 (pp. 55–58) Sjoberg.

*Primary Examiner*—John M. Ford
*Attorney, Agent, or Firm*—Michele A. Kovaleski

[57] ABSTRACT

An improved process for the preparation of 2,4-di(alkylamino)-6-alkylthio-s-triazines wherein cyanuric chloride is reacted in successive steps with two appropriate alkylamines and an alkyl mercaptan is described where the improvement involves use of a single water-immiscible solvent and a phase transfer catalyst in the mercaptan addition step.

11 Claims, No Drawings

PROCESS FOR THE PREPARATION OF 2,4-DI(ALKYLAMINO)-6-ALKYLTHIO-S-TRIAZINES

The present invention relates to an improved process for the preparation of 2,4-di(alkylamino)-6-alkylthio-s-triazines or of 2-alkylamino-4,6-dialkylthio-s-triazines, wherein cyanuric chloride is reacted in three successive steps with two appropriate alkylamines and an alkyl mercaptan, or in the alternative, with an appropriate alkylamine and two alkyl mercaptans where the improvement involves the use of a single water-immiscible solvent and a phase transfer catalyst in the mercaptan addition step.

The preparation of substituted 2,4-diamino-6-alkylthio-s-triazines by successive three-step addition processes to cyanuric chloride is known. Thus, similar three-step processes are described in U.S. Pat. Nos. 3,830,810; 3,766,182; and 3,753,986 in which, in the first two successive reaction steps, cyanuric chloride is reacted with one primary amine followed by reaction with a second primary amine in a solvent or diluent such as aliphatic hydrocarbons, ketones, ethers, aromatic hydrocarbons, etc., and in the presence of an acid-binding agent, with the first stage (i.e., addition of the first amine) being carded out at temperatures below 30° C., preferably between −15° and 0° C., and the second amination at temperatures of between 0° and 45° C. The replacement of the last chlorine atom by the alkylthio radical is performed by a process in which an aqueous base solution is added to the suspension of the intermediate in a diluent (i.e., in acetone/water), and the mixture subsequently stirred until a clear solution is formed. A double molar amount of alkyl mercaptan is then introduced, the whole stirred at room temperature, and the desired product isolated.

Alternatively, said prior art references provide that exchange of the last chlorine for the alkylthio radical can also be effected by the addition of the corresponding 6-chloro-s-triazine derivative to an alcoholic or alcoholic/aqueous solution of an alkali metal mercaptide, and the refluxing of the resulting mixture until it becomes neutral.

The principal disadvantage of these known processes for the synthesis of 2,4-di(alkylamino)-6-alkylthio-s-triazines is that the intermediate obtained after the second step must be isolated and/or purified, e.g., by means of filtration or recrystallization, before being reacted further if the final product is to be obtained in an acceptable yield. However, isolation of the intermediate 2,4-diamino-6-chloro-s-triazine entails losses in yield, is economically undesirable and time-consuming, and results in adverse environmental pollution.

An additional significant disadvantage of these known processes is the need to change solvents, for e.g., toluene in the first two addition steps followed by its removal and replacement by an acetone/water diluent for exchange of the final chlorine atom. Such solvent replacement leads to increased cycle times, higher product costs, higher effluent loading and increased environmental pollution. Moreover, the acetone/water mixture renders the removal of sodium chloride from the final product difficult.

Alternatively, a process for the preparation of 2-alkylthio-4,6-diamino-s-triazines is disclosed in U.S. Pat. No. 3,629,256, wherein cyanuric chloride is reacted in successive steps, first with an alkylamine, second with an alkyl mercaptan, and third with a cycloalkylamine. Each of the three steps is carried out in the presence of an acid-binding agent and using a water/acetone mixture. Significant disadvantages are associated with the above process, mainly that a temperature of below 0° C. (i.e., between 0 and −10° C.) is needed in the first step to achieve good selectivity of the amine onto the triazine ring. Moreover, difficulties may be encountered with removal of sodium chloride from the final product and with solvent recovery due to the presence of the acetone/water diluent.

Surprisingly, a process for the preparation of 2,4-di(alkylamino)-6-alkylthio-s-triazines has now been found which eliminates the need to isolate and/or purify intermediate products and the need to change solvents during manufacture. The instant process, which employs a single water-immiscible solvent or a mixture thereof in all three addition steps coupled with a phase transfer catalyst in the alkyl mercaptan addition step, reduces cycle times, reduces environmental emissions by the elimination of the number of solvents used for production and makes facile the removal of sodium chloride from the final product. Additionally, the instant process overcomes the problem of requiring temperatures of less than 0° C. to attain good selectivity onto the triazine ring. From the foregoing, it is clear that the outlays in terms of time, energy and material, as well as the generation of waste, are greatly diminished.

DETAILED DESCRIPTION OF THE INVENTION

The present invention therefore relates to an improved process for the preparation of compounds of formula (I) or formula II)

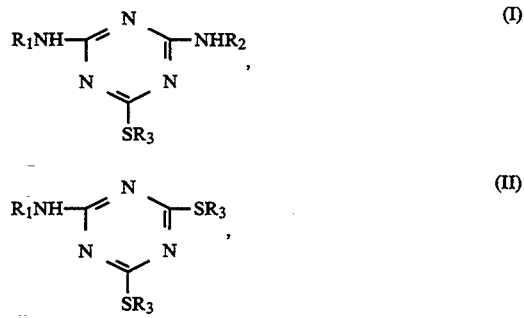

wherein $R_1$ and $R_2$ are independently hydrogen, alkyl of 1 to 12 carbon atoms, cycloalkyl of 3 to 12 carbon atoms, said cycloalkyl substituted by alkyl groups of 1 to 4 carbon atoms, cycloalkyl-alkyl of 4 to 20 carbon atoms, said cycloalkyl-alkyl of 4 to 20 carbon atoms substituted by alkyl groups of 1 to 4 carbon atoms, aryl of 6 to 10 carbon atoms, said aryl substituted by 1 to 3 alkyl groups of 1 to 4 carbon atoms, phenylalkyl of 7 to 15 carbon atoms, said phenylalkyl substituted by 1 to 3 alkyl groups of 1 to 4 carbon atoms, alkoxyalkyl of 2 to 14 carbon atoms, cyanoalkyl of 2 to 13 carbon atoms, alkenyl of 3 to 12 carbon atoms, alkynyl of 3 to 12 carbon atoms, furfuryl or tetrahydrofurfuryl; and $R_3$ is an alkyl of 1 to 12 carbon atoms, phenyl or phenylalkyl of 7 to 15 carbon atoms, by the reaction of cyanuric chloride in successive steps with $R_1NH_2, R_2NH_2$ and $R_3SH$ or with $R_1NH_2$ and $R_3SH$, being carried out in the presence of an acid-binding agent and in an organic solvent wherein the improvement comprises:

(a) carrying out the reaction sequence in a single water-immiscible organic solvent or a mixture of two or more water-immiscible organic solvents, wherein the solvent is an aliphatic hydrocarbon of 7 to 11 carbon atoms, a cycloalkane of 6 to 10 carbon atoms, an aromatic hydrocarbon of 6 to 10 carbon atoms, an alkanone of 4 to 11 carbon atoms or a dialkyl ether of 6 to 10 carbon atoms; and (b) employing an effective amount of a phase transfer catalyst selected from the group consisting of quaternary ammonium salts, quaternary phosphonium salts, diazacycloalkanes and crown ethers.

The first and second aminations of the instant process are carried out in an organic solvent, in a manner known per se. Suitable organic solvents are aliphatic hydrocarbons of 7 to 11 carbon atoms, cycloalkanes of 6 to 10 carbon atoms, aromatic hydrocarbons of 6 to 10 carbon atoms, alkanones of 4 to 11 carbons, dialkyl ethers of 6 to 10 carbon atoms. Especially suitable organic solvents are heptane, octane, nonane, decane, undecane, cyclohexane, benzene, toluene, xylene, mesitylene, methyl ethyl ketone, methyl isobutyl ketone, amyl ethyl ketone, propyl ether, butyl ethyl ether, butyl ether, pentyl ether and isoamyl ether and in particular, toluene and xylene, with xylene being the most preferred.

In the mercaptan addition step, an effective amount of phase transfer catalyst is employed in the range of from 1 to 10 mole percent, based on initial cyanuric chloride, which is selected from the group comprising quaternary ammonium salts, quaternary phosphonium salts, diazacycloalkanes and crown ethers. Especially suitable phase transfer catalysts are tributylmethylammonium chloride, 1,4-diazabicyclo[2.2.2]octane, benzyltrimethylammonium hydroxide, tetrabutylammonium chloride, tetrabutylammonium bromide and tetrabutylammonium hydrogen sulfate, and in particular, tetrabutylammonium bromide.

Appropriate amines to be used in the instant process are of the formula $R_1NH_2$ and $R_2NF_2$, wherein $R_1$ and $R_2$ are independently hydrogen, alkyl of 1 to 12 carbon atoms, cycloalkyl of 3 to 12 carbon atoms, said cycloalkyl substituted by alkyl groups of 1 to 4 carbon atoms, cycloalkyl-alkyl of 4 to 20 carbon atoms, said cycloalkyl-alkyl of 4 to 20 carbon atoms substituted by alkyl groups of 1 to 4 carbon atoms, aryl of 6 to 10 carbon atoms, said aryl substituted by 1 to 3 alkyl groups of 1 to 4 carbon atoms, phenylalkyl of 7 to 15 carbon atoms, said phenylalkyl substituted by 1 to 3 alkyl groups of 1 to 4 carbon atoms, alkoxyalkyl of 2 to 14 carbon atoms, cyanoalkyl of 2 to 13 carbon atoms, alkenyl of 3 to 12 carbon atoms, alkynyl of 3 to 12 carbon atoms, furfuryl or tetrahydrofurfuryl. Preferably, $R_1$ and $R_2$ are independently hydrogen, alkyl of 1 to 12 carbon atoms, cycloalkyl of 3 to 12 carbon atoms, or said cycloalkyl substituted by alkyl groups of 1 to 4 carbon atoms. More preferably, $R_1$ is a cycloalkyl of 3 to 12 carbon atoms and $R_2$ is an alkyl of 1 to 12 carbon atoms. Most preferably, $R_1$ is cyclopropyl and $R_2$ is tert-butyl.

Appropriate alkyl mercaptans to be used in the instant process are of the formula $R_3SH$, wherein $R_3$ is an alkyl of 1 to 12 carbon atoms, phenyl or phenylalkyl of 7 to 15 carbon atoms. Preferably, $R_3$ is an alkyl of 1 to 12 carbon atoms, and in particular, methyl.

To obtain the compounds of formula (I), the rust step of the instant process involves reaction of cyanuric chloride with an appropriate alkylamine in a 1:1 molar ratio based on cyanuric chlride at 0°–75° C., preferably, between 20° and 50° C., in an organic solvent and in the presence of an acid-binding agent in order to neutralize the hydrochloric acid produced. A broad pH range (i.e., 1–9) may be used, but preferably, the pH value is between 6.5 and 8.0, in order to avoid the formation of hydrolytic products. Said reaction is complete when a pH of approximately 7 is maintained without the need for additional acid-binding agent.

In the next step of the instant process, a second amine in a 1:1 molar ratio based on initial cyanuric chloride is added to the first step intermediate product/organic solvent solution at 20°–95° C., and preferably, at between 50° and 75° C. An acid-binding agent is simultaneously introduced to neutralize the hydrochloric acid produced. A broad pH range (i.e., between 4 and 12) may be used, but preferably, the pH value is between 8 and 10 in order to avoid the formation of hydrolytic products. Said reaction is complete when a pH of approximately 9 is maintained without the need for additional acid-binding agent.

In the third step involving exchange of the final chlorine, an appropriate phase transfer catalyst in a range of 1 to 10 mole percent, based on initial cyanuric chloride, acid-binding agent and mercaptan in a 1.0–1.3:1 molar ratio, based on initial cyanuric chloride, are added to the second step reaction solution. Said reaction is carried out at a temperature of between 60° and 150° C. and at a pressure of between atmospheric and 100 psig (atmospheric - 7 kg/cm$^2$). However, preferably, the temperature is between 90° and 130° C., and the preferable pressure range is between atmospheric and 50 psig (atmospheric - 3.5 kg/cm$^2$).

To obtain the compounds of formula (II), step 1 is carried out as set forth hereinabove. In the next step involving exchange of the last two chlorine atoms, an appropriate phase transfer catalyst in the range of from 1 to 10 mole percent, based on initial cyanuric chloride, acid-binding agent and mercaptan in a 2.0–2.6:1 molar ratio, based on initial cyanuric chloride, are added to the step one reaction solution. Said reaction is carded out at a temperature of between 60° and 150° C. and at a pressure of between atmospheric and 100 psig (atmospheric 7 kg/cm$^2$). Preferably, the temperature is between 90° and 130° C., and the preferable pressure range is between atmospheric and 50 psig (atmospheric - 3.5 kg/cm).

Applicable as acid-binding agents for these reactions are inorganic bases such as alkali metal hydroxides or carbonates and alkaline earth metal hydroxides or carbonates, an excess of the alkylamine to be reacted, and tertiary amines such as trialkylamines, pyridine and pyridine bases. Inorganic bases, particularly the alkali metal hydroxides such as sodium hydroxide, are preferred. If an organic base is used, the organic solvent should be washed with water, followed by neutralizing the resulting waste water and then recovering the organic base.

Di(alkylamino)-alkylthio-s-triazine derivatives are well known to exhibit herbicidal and algaecidal activity and are particularly useful for the selective control of weeds and wild grasses and as antifouling agents.

The improved process according to the instant invention for the production of the s-triazines of formula (I) and formula (II) is illustrated by the following examples. Unless stated otherwise, pans and percentages are by weight in said Examples. The products of the Examples are compared to authentic pure known samples of the respective compounds by gas chromatography as a measure of product purity.

EXAMPLE 1

2-(tert-Butylamino)-4-(cyclopropylamino)-6-(methylthio)-s-triazine

Step 1: In a reaction flask purged with nitrogen and sealed, cyanuric chloride (92.3 g, 0.5 mole) is reacted with tert-butylamine (36.9 g, 0.5 mole), using o-xylene (370 g) as the solvent. The amine is added over a period of 30 minutes. Then, a 20% sodium hydroxide solution (98.8 g, 0.49 mole) is added over a period of 90 minutes to maintain the pH at a value between 6.5 and 8.0 at a temperature of 50°C. The reaction is complete when a stable pH of approximately 7 is reached.

Step 2: Cyclopropylamine (39.6 g, 0.5 mole) is added over a period of 10–15 minutes to the step 1/o-xylene solution at 50° C. By the end of the amine addition, the reaction temperature is 70°–75° C. A 20% sodium hydroxide solution (98.8 g, 0.49 mole) is added over a period of 30 minutes to maintain the pH at a value between 8 and 10 at a temperature of 75° C. The reaction is complete when a stable pH of approximately 9 is reached.

Upon completion of the step 2 reaction, the aqueous and organic layers are allowed to separate, and a brine split is made. The organic step 2 solution is concentrated to 50% by weight by azeotropic or vacuum distillation of o-xylene.

Step 3: The step 2 reaction mass (236 g), tetrabutylammonium bromide (3.18 g, 0.01 mole) and 20% sodium hydroxide solution (108.4 g, 0.54 mole) are added to a stainless steel Parr reactor. The resulting reaction mixture is cooled to 0° C., and the reactor is purged with nitrogen and sealed. At 0° C., methyl mercaptan (27.2 g, 0.57 mole) is added, and the reaction mixture is then heated to 100° C. over 30 minutes. At 100° C., the pressure in the reactor is 15–20 psig (1.1–1.4 kg/cm$^2$), and the reactor is held at these conditions for four hours with agitation.

After completion of the step 3 reaction, the pressure is vented, and the brine layer is split off. The organic layer is washed twice with water (100 g per wash) and split off. Water (600 g) is then added to the organic layer, and the solvent is removed by azeotropic distillation. Naphthalene-sulfonic acid-formaldehyde, sodium salt (0.7 g), a dispersant, is added to aid precipitation of the final product in hot water. The slurry is cooled to 50° C. and filtered. After washing the filter cake with water (500 g), it is dried under vacuum at 75° C., yielding 124.1 g of a white solid, 96.0% based on cyanuric chloride, as is.

Other suitable dispersants to be used in place of the naphthalene-sulfonic acid-formaldehyde are sulfated propyloleate, sulfated butyloleate, N-methyl-N-oleoyl-taurate and N-methyl-N-oleoyl-taurate.

Analysis: 98.2% pure compared to a standard sample of the title compound as carried out by gas chromatography on a Hewlett Packard 5890 equipped with a DB-5 (30 meters long, megabore, 1 micron film thickness) column.

EXAMPLE 2

2-(tert-Butylamino)-4-(cyclopropylamino)-6-(methylthio)-s-triazine

The procedure described in Example 1 is followed except methyl isobutyl ketone is substituted for o-xylene. The product is obtained in 96% of theory as a white solid. Gas chromatography shows the product to be 97.2% pure.

EXAMPLE 3

2-(tert-Butylamino)-4-(cyclopropylamino)-6-(methylthio)-s-triazine

The procedure described in Example 2 is followed except no phase transfer catalyst is added to the Step 3 reaction. After four hours, the Step 3 reaction mass is analyzed by gas chromatography, and the following results are obtained:

2-(tert-butylamino)-4-(cyclopropylamino)-6-(methylthio)-s-triazine=70%; and 2-(tert-butylamino)-4-chloro-6-(methylthio)-s-triazine=30%.

It is clear that without the phase transfer catalyst, the reaction does not go to completion.

EXAMPLE 4

2-(tert-Butylamino)-4-(cyclopropylamino)-6-(methylthio)-s-triazine

Step 1: In a reaction flask purged with nitrogen and sealed, cyanuric chloride (92.3 g, 0.5 mole) is reacted with tert-butylamine (36.9 g, 0.5 mole), using toluene (370 g) as the solvent. The amine is added over a period of 30 minutes. Then, a 20% sodium hydroxide solution (98.8 g, 0.49 mole) is added over a period of 90 minutes to maintain the pH at a value between 6.5 and 8.0 at a temperature of 50° C. The reaction is complete when a stable pH of approximately 7 is reached.

Step 2: Cyclopropylamine (39.6 g, 0.5 mole) is added over a period of 10–15 minutes to the step 1/toluene solution at 50° C. By the end of the amine addition, the reaction temperature is 70°–75° C. A 20% sodium hydroxide solution (98.8 g, 0.49 mole) is added over a period of 30 minutes to maintain the pH at a value between 8 and 10 at a temperature of 75° C. The reaction is complete when a stable pH of approximately 9 is reached.

Upon completion of the step 2 reaction, the aqueous and organic layers are allowed to separate, and a brine split is made. The organic step 2 solution is concentrated to 50% by weight by azeotropic or vacuum distillation of toluene.

Step 3: The step 2 reaction mass (236 g), tributylmethylammonium chloride (12.36 g, 0.039 mole) and 20% sodium hydroxide solution (108.4 g, 0.54 mole) are added to a stainless steel Parr reactor. The resulting reaction mixture is cooled to 0° C., and the reactor is purged with nitrogen and sealed. At 0° C., methyl mercaptan (27.2 g, 0.57 mole) is added, and the reaction mixture is then heated to 100° C. over 30 minutes. At 100° C., the pressure in the reactor is 15–20 psig (1.1–1.4 kg/cm$^2$), and the reactor is held at these conditions for four hours with agitation.

After completion of the step 3 reaction, the pressure is vented, and the brine layer is split off. The organic layer is washed once with water (100 g) and split off. Water (1,200 g) is then added to the organic layer, and the solvent is removed by azeotropic distillation.

The slurry is cooled to 50° C. and filtered. After washing the filter cake with water (400 g), it is dried under vacuum at 80° C., yielding 119.2 g, 96.6% of theory.

Analysis: 97.4% pure by gas chromatography.

EXAMPLE 5

2-(tert-Butylamino)-4-(cyclopropylamino)-6-(methylthio)-s-triazine

The procedure described in Example 1 is followed except 1,4-diazabicyclo[2.2.2]octane (4.94 g, 0.043 mole) is used as the the Step 3 phase transfer catalyst instead of the tetrabutylammonium bromide. The product is obtained in 97.2% of theory as a white solid. Gas chromatography shows the product to be 97.3% pure.

EXAMPLE 6

2-(tert-Butylamino)-4-(cyclopropylamino)-6-(methylthio)-s-triazine

The procedure described in Example 1 is followed except tetrabutylammonium hydrogen sulfate (3.31 g, 0.0098 mole) is used as the Step 3 phase transfer catalyst in place of the tetrabutylammonium bromide. The product is obtained in 97.9% of theory as a white solid. Gas chromatography shows the product to be 97.5% pure.

EXAMPLE 7

2-(tert-Butylamino)-4-(cyclopropylamino)-6-(methylthio)-s-triazine

The procedure described in Example 1 is followed except benzyltrimethylammonium hydroxide (8.4 g, 0.02 mole) is used as the Step 3 phase transfer catalyst in place of the tetrabutylammonium bromide. The product is obtained in 95.9% of theory as a white solid. Gas chromatography shows the product to be 97.5% pure.

EXAMPLE 8

2,4-bis(tert-Butylamino)-6-(methylthio)-s-triazine

Steps 1 and 2: In a reaction flask purged with nitrogen and sealed, cyanuric chloride (50 g, 0.27 mole) is reacted with tert-butylamine (40.3 g, 0.54 mole), using methyl isobutyl ketone as the solvent. The amine is added over a period of 30 minutes. Then, a 20% sodium hydroxide solution (108 g, 0.54 mole) is added over a period of 150 minutes to maintain a pH at a value between 8.0 and 10.0 at a temperature of 55°–75° C. The reaction is complete when a stable pH of approximately 9 is reached.

Upon completion of the step 2 reaction, the aqueous and organic layers are allowed to separate, and a brine split is made. The organic step 2 solution is concentrated to 40% by weight by azeotropic distillation of methylisobutyl ketone.

Step 3: The step 2 reaction mass (173 g), tetrabutylammonium bromide (7.35 g, 0.023 mole) and 20% sodium hydroxide solution (60.0 g, 0.3 mole) are added to a stainless steel Parr reactor. The resulting reaction mixture is cooled to 0°C., and the reactor is purged with nitrogen and sealed. At 0° C., methyl mercaptan (16 g, 0.33 mole) is added, and the reaction mixture is then heated to 100° C. over 30 minutes. At 100° C., the pressure in the reactor is 45–50 psig (3.2–3.5 kg/cm$^2$), and the reactor is held at these conditions for six hours with agitation.

After completion of the step 3 reaction, the pressure is vented, and the brine layer is split off. The organic layer is washed once with water (350 g) and split off. Water (1,000 g) is then added to the organic layer, and the solvent is removed by azeotropic distillation. The slurry is cooled to 50° C. and filtered. After washing the cake with water (300 g), it is dried under vacuum at 80° C., yielding a white product with a melting point of 169°–170° C. Gas chromatography shows the product to be 96.0% pure.

EXAMPLE 9

2,4-bis(Cyclopropylamino)-6-(methylthio)-s-triazine

Steps 1 and 2: In a reaction flask purged with nitrogen and sealed, cyanuric chloride (92.3 g, 0.5 mole) is reacted with cyclopropylamine (78.0 g, 1.0 mole), using methyl isobutyl ketone as the solvent. The amine is added over a period of 30 minutes. Then, a 20% sodium hydroxide solution (203.3 g, 1.0 mole) is added over a period of 165 minutes to maintain the pH at a value between 8.0 and 10.0 at a temperature of 75° C. The reaction is complete when a stable pH of approximately 9 is reached.

Upon completion of the step 2 reaction, the aqueous and organic layers are allowed to separate, and a brine split is made. The organic step 2 solution is concentrated to 44% by weight by azeotropic distillation of methyl isobutyl ketone.

Step 3: The step 2 reaction mass (233 g), tetrabutylammonium bromide (12.79 g, 0.04 mole) and 20% sodium hydroxide solution (101.4 g, 0.51 mole) are added to a stainless steel Parr reactor. The resulting reaction mixture is cooled to 0° C., and the reactor is purged with nitrogen and sealed. At 0° C., methyl mercaptan (30 g, 0.63 mole) is added, and the reaction mixture is then heated to 100° C. over 25 minutes. At 100° C., the pressure in the reactor is 30–35 psig (2.1–2.5 kg/cm$^2$), and the reactor is held at these conditions for six hours with agitation.

After completion of the step 3 reaction, the pressure is vented, and the brine layer is split off. The organic layer is washed once with water (300 g) and split off. Water (800 g) is then added to the organic layer, and the solvent is removed by azeotropic distillation. The slurry is cooled to 50° C. and filtered. After washing the cake with water (300 g), it is dried under vacuum at 80° C., yielding a white product with a melting point of 114°–116° C. Gas chromatography shows the product to be 96.6% pure.

EXAMPLE 10

2-Amino-4-tert-butylamino-6-methylthio-s-triazine

Step 1: In a reaction flask purged with nitrogen and sealed, cyanuric chloride (65.5 g, 0.36 mole) is reacted with tert-butylamine (26.5 g, 0.36 mole), using o-xylene (260 g) as the solvent. The amine is added over a period of 30 minutes. Then, a 20% sodium hydroxide solution (71.0 g, 0.36 mole) is added over a period of 150 minutes to maintain the pH at a value between 6.5 and 8.0 at a temperature of 50° C. The reaction is complete when a stable pH of approximately 7 is reached.

Step 2: Ammonia (29%, 41.6 g, 0.71 mole) is added over a period of 30 minutes to the step 1 o-xylene solution at 50° C. At the end of the addition, the temperature is raised to 75° C. After the reaction is complete, the aqueous layer is split. The step 2/o-xylene solution is washed once with water (230 g) and split off. The organic step 2 solution is concentrated to 45% by weight by azeotropic distillation of o-xylene.

Step 3: The step 2 reaction mass (131 g), tetrabutylammonium bromide (9.0 g, 0.028 mole) and 20% sodium hydroxide solution (70 g, 0.35 mole) are added to a stainless steel Parr reactor. The resulting reaction mixture is cooled to 0° C., and the reactor is purged with nitrogen and sealed. At 0° C., methyl mercaptan (20 g, 0.42 mole) is added, and the reaction mixture is then heated to 100° C. over 20 minutes. At 100° C., the pressure in the reactor is 37 psig (2.59 kg/cm$^2$), and the reactor is held at these conditions for four hours with agitation.

After completion of the step 3 reaction, the pressure is vented, and the brine layer is washed once with water (100 g) and split off. Water (600 g) is then added to the organic layer, and the solvent is removed by azeotropic distillation. The slurry is cooled to 50° C. and filtered. After washing the cake with water (300 g), it is dried under vacuum at 80° C., yielding 53.3 g of a white solid, 70.6% of theory with a melting point of 143°–145° C. Gas chromatography shows the desired product to be 99% pure.

EXAMPLE 11

2-tert-Butylamino-4,6-bis(methylthio)-s-triazine

Step 1: In a reaction flask purged with nitrogen and sealed, cyanuric chloride (92.3 g, 0.5 mole) is reacted with tert-butylamine (37.2 g, 0.5 mole), using o-xylene (379 g) as the solvent. The amine is added over a period of 30 minutes. Then, a 20% sodium hydroxide solution (98.8 g, 0.49 mole) is added over a period of 90 minutes to maintain the pH at a value between 6.5 and 8.0 at a temperature of 50° C. The reaction is complete when a stable pH of approximately 7 is reached.

Upon completion of the step 1 reaction, the aqueous and organic layers are allowed to separate, and a brine split is made. The organic step 1 solution is concentrated to 50% by weight by vacuum distillation of o-xylene.

Steps 2 and 3: The step 1 reaction mass (222 g), tetrabutylammonium chloride (17.7 g, 0.06 mole) and 20% sodium hydroxide solution (216.8 g, 1.08 mole) are added to a stainless steel Parr reactor. The resulting reaction mixture is cooled to 0° C., and the reactor is purged with nitrogen and sealed. At 0° C., methyl mercaptan (55 g, 1.15 mole) is added, and the reaction mixture is then heated to 100° C. over 30 minutes. At 100° C., the pressure in the reactor is 15–20 psig (1.1–1.4 kg/cm$^2$), and the reactor is held at these conditions for four hours with agitation.

After completion of the step 3 reaction, the pressure is vented, and the brine layer is split off. The organic layer is washed once with water and twice with 5% hydrochloric acid (200 g per wash) and split off. Water (800 g) is then added to the organic layer, and the solvent is removed by azeotropic distillation.

The product oil is split from the hot water and dried in a vacuum oven at 70° C. The product solidifies upon cooling, yielding a white solid, 87% of theory, with a melting point of 67°–68° C. Gas chromatography shows the desired product to be 99% pure.

EXAMPLE 12–20

Using the general procedure of Example 1, the following compounds are produced:
2-(ethylamino)-4-(methylthio)-6-(tetrahydrofurfurylamino )-s-triazine;
2-(tert-butylamino)-4-(methylthio)-6-(tetrahydrofurfurylamino)-s-triazine;
2-(ethylamino)-4-(isopropylamino)-6-(methylthio)-s-triazine;
2-(tert-butylamino)-4-(cyclopropylamino)-6-(methylthio)-s-triazine;
2-(tert-butylamino)-4-(cyclopropylamino)-6-(phenylthio)-s-triazine;
2-(methylamino)-4-(cyclopropylmethylamino)-6-(butylthio)-s-triazine;
2-(octylamino)-4-(cyclobutylamino)-6-(pentylthio)-s-triazine;
2-(amylamino)-4-(cyclohexylamino)-6-(hexylthio)-s-triazine; and
2-(hexylamino)-4-(methylamino)-6-(ethylthio)-s-triazine.

EXAMPLE 21–29

Using the general procedure of Example 8, the following compounds are produced:
2,4-bis(isopropylamino)-6-(methylthio)-s-triazine;
2,4-bis(dodecylamino)-6-(methylthio)-s-triazine;
2,4-bis(benzylamino)-6-(methylthio)-s-triazine;
2,4-bis(benzylamino)-6-(benzylthio)-s-triazine;
2,4-bis(anilino)-6-(phenylthio)-s-triazine;
2,4-bis(tert-butylamino)-6-(ethylthio)-s-triazine;
2,4-bis(amylamino)-6-(hexylthio)-s-triazine;
2,4-bis(ethylamino)-6-(butylthio)-s-triazine; and
2,4-bis(octylamino)-6-(propylthio)-s-triazine.

EXAMPLES 30–35

Using the general procedure of Example 10, the following compounds are produced;
2-(amino)-4-(tert-butylamino)-6-(methylthio)-s-triazine;
2-(amino)-4-(dodecylamino)-6-(methylthio)-s-triazine;
2-(amino)-4-(isopropylamino)-6-(benzylthio)-s-triazine;
2-(amino)-4-(cyclopropylamino)-6-(hexylthio)-s-triazine;
2-(amino)-4-(octylamino)-6-(decylthio)-s-triazine; and
2-(amino)-4-(methylamino)-6-(nonylthio)-s-triazine.

EXAMPLES 36–46

Using the general procedure of Example 11, the following compounds are produced:
2-(tert-butylamino)-4,6-bis(methylthio)-s-triazine;
2-(cyclopropylamino )-4,6- bis(methylthio)-s-triazine;
2-(amino)-4,6-bis(methylthio)-s-triazine;
2-(amino)-4,6-bis(phenylthio)-s-triazine;
2-(dodecylamino)-4,6-bis(n-butylthio)-s-triazine;
2-(ethylamino)-4,6-bis(benzylthio)-s-triazine;
2-(decylamino)-4,6-bis(ethylthio)-s-triazine;
2-(anilino)-4,6-bis(methylthio)-s-triazine;
2-(amylamino)-4,6-bis(hexylthio)-s-triazine;
2-(cyclobutylamino)-4,6-bis(pentylthio)-s-triazine; and
2-(cyclohexyl)-4,6-bis(butylthio)-s-triazine.

What is claimed is:

1. An improved process for the preparation of compounds of formula (I) or formula (II)

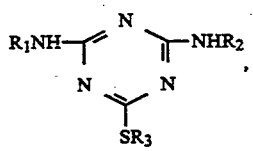

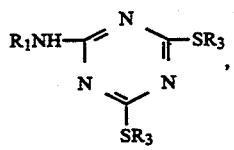

wherein R$_1$ and R$_2$ are independently hydrogen, alkyl of 1 to 12 carbon atoms, cycloalkyl of 3 to 12 carbon atoms, said cycloalkyl substituted by alkyl groups of 1 to 4 carbon atoms, cycloalkyl-alkyl of 4 to 20 carbon atoms, said cycloalkyl-alkyl of 4 to 20 carbon atoms substituted by alkyl groups of 1 to 4 carbon atoms, aryl of 6 to 10 carbon atoms, said aryl substituted by 1 to 3 alkyl groups of 1 to 4 carbon atoms, phenylalkyl of 7 to 15 carbon atoms, said phenylalkyl substituted by 1 to 3 alkyl groups of 1 to 4 carbon atoms, alkoxyalkyl of 2 to 14 carbon atoms, cyanoalkyl of 2 to 13 carbon atoms, alkenyl of 3 to 12 carbon atoms, alkynyl of 3 to 12 carbon atoms, furfuryl or tetrahydrofurfuryl; and $R_3$ is an alkyl of 1 to 12 carbon atoms, phenyl or phenylalkyl of 7 to 15 carbon atoms, by the reaction of cyanuric chloride in successive steps with $R_1NH_2, R_2NH_2$ and $R_3SH$ or with $R_1NH_2$ and $R_3SH$, being carried out in the presence of an acid-binding agent and in an organic solvent wherein the improvement comprises:

(a) carrying out the reaction sequence in a single water-immiscible organic solvent or a mixture of two or more water-immiscible organic solvents, wherein the solvent is an aliphatic hydrocarbon of 7 to 11 carbon atoms, a cycloalkane of 6 to 10 carbon atoms, an aromatic hydrocarbon of 6 to 10 carbon atoms, an alkanone of 5 to 11 carbon atoms or a dialkyl ether of 6 to 10 carbon atoms; and (b) employing an effective amount of a phase transfer catalyst selected from the group consisting of quaternary ammonium salts, quaternary phosphonium salts, and crown ethers.

2. A process according to claim 1, wherein the reaction is carried out using heptane, octane, nonane decane, undecane, cyclohexane, benzene, toluene, xylene, mesitylene, methyl isobutyl ketone, amyl ethyl ketone, propyl ether, butyl ethyl ether, butyl ether, pentyl ether or isoamyl ether as the organic solvent.

3. A process according to claim 2, wherein the reaction is carried out using xylene or toluene as the organic solvent.

4. A process according to claim 3, wherein the reaction is carded out using xylene.

5. A process according to claim 1, wherein component (b) is employed in an amount ranging from from about 1 to 10 mole percent, based on initial cyanuric chloride.

6. A process according to claim 1, wherein the phase transfer catalyst is tributylmethylammonium chloride, benzyltrimethylammonium hydroxide, tetrabutylammonium chloride, tetrabutylammonium bromide or tetrabutylammonium hydrogen sulfate.

7. A process according to claim 6, wherein, the phase transfer catalyst is tetrabutylammonium bromide.

8. A process according to claim 1, wherein $R_1$ and $R_2$ are independently hydrogen, an alkyl of 1 to 12 carbon atoms, cycloalkyl of 3 to 12 carbon atoms or said cycloalkyl substituted by alkyl groups of 1 to 4 carbon atoms.

9. A process according to claim 1, wherein, in formula (I), $R_1$ is a cycloalkyl of 3 to 12 carbon atoms, $R_2$ is an alkyl of 1 to 12 carbon atoms and $R_3$ is an alkyl of 1 to 12 carbon atoms.

10. A process according to claim 9, wherein, in formula (I), $R_1$ is cyclopropyl, $R_2$ is tert-butyl and $R_3$ is methyl.

11. A process according to claim 1, wherein the compounds of formula (I) or formula (II) are 2-(tert-butylamino)-4-(cyclopropylamino)-6-(methylthio)-s-triazine, 2,4-bis(tert-butylamino)-6-(methylthio)-s-triazine, 2,4-bis(cyclopropylamino)-6-(methylthio)-s-triazine, 2-amino-4-tert-butylamino-6-methylthio-s-triazine and 2-tert-butylamino-4,6-bis(methylthio)-s-triazine.

* * * * *